United States Patent [19]

Schweich, Jr. et al.

[11] Patent Number: 5,782,797
[45] Date of Patent: Jul. 21, 1998

[54] THERAPEUTIC INFUSION DEVICE

[75] Inventors: Cyril J. Schweich, Jr., St. Paul; Julie A. Brunner, Woodbury; Todd J. Mortier, Minneapolis, all of Minn.

[73] Assignee: SCIMED Life Systems, Inc., Maple Grove, Minn.

[21] Appl. No.: 659,462

[22] Filed: Jun. 6, 1996

[51] Int. Cl.$^6$ .................................................. A61M 31/00
[52] U.S. Cl. ........................... 604/49; 604/264; 604/280
[58] Field of Search ............................ 604/21, 27, 28, 604/48, 49, 52, 53, 93, 96, 102, 158, 164, 264, 280, 281

[56] References Cited

U.S. PATENT DOCUMENTS

| | | | |
|---|---|---|---|
| 4,568,329 | 2/1986 | Mahurkar | 604/43 |
| 4,626,240 | 12/1986 | Edelman et al. | 604/43 |
| 4,641,654 | 2/1987 | Samson et al. | |
| 4,776,841 | 10/1988 | Catalano | 604/43 |
| 4,968,306 | 11/1990 | Huss et al. | |
| 4,968,307 | 11/1990 | Dake et al. | 604/264 |
| 5,009,636 | 4/1991 | Wortley et al. | 604/43 |
| 5,050,606 | 9/1991 | Tremulis | |
| 5,207,648 | 5/1993 | Gross | |
| 5,211,636 | 5/1993 | Mische | |
| 5,221,256 | 6/1993 | Mahurkar | 604/43 |
| 5,250,034 | 10/1993 | Appling et al. | |
| 5,322,508 | 6/1994 | Viera | 604/52 |
| 5,324,253 | 6/1994 | McRea et al. | 604/282 |
| 5,356,388 | 10/1994 | Sepetka et al. | |
| 5,364,344 | 11/1994 | Beattie et al. | 604/43 |
| 5,380,276 | 1/1995 | Miller et al. | 604/28 |
| 5,409,455 | 4/1995 | Belden | |
| 5,569,197 | 10/1996 | Helmus et al. | 604/96 |
| 5,569,215 | 10/1996 | Crocker | 604/264 |
| 5,624,396 | 4/1997 | McNamara et al. | 604/93 |
| 5,626,564 | 5/1997 | Zhan et al. | 604/164 |
| 5,626,601 | 5/1997 | Gershony et al. | 604/194 |

FOREIGN PATENT DOCUMENTS 0 535 874 A1  7/1993  European Pat. Off.

OTHER PUBLICATIONS

Tracker ®–18 Unibody ® Infusion Catheter Product Sheet, Target Therapeutics.

Primary Examiner—Mark Bockelman
Assistant Examiner—Cris L. Rodriguez
Attorney, Agent, or Firm—Luke Dohmen

[57] ABSTRACT

A method of treating an acute occlusion of the human vasculature as in stroke. The method includes providing a device flexible enough to be steered within the tortuous anatomy and still have the ability to be pushed across a thrombic occlusion. The device further provides two distinct sets of infusion lumens. The method includes advancing the device through the vasculature such that one infusion lumen is located distal to the thrombic occlusion and the other infusion lumen is located proximal to the occlusion. A neuroprotective drug is then infused through an opening distal to the occlusion and a thrombolytic agent infused through an opening proximal to the occlusion thereby dissolving the occlusion while minimizing damage to tissues distal to the occlusion.

14 Claims, 4 Drawing Sheets

THERAPEUTIC INFUSION DEVICE

FIELD OF THE INVENTION

The present invention generally relates to treatment of occluded vessels. More specifically the invention relates to minimally invasive devices used to treat sudden occlusion of small and tortuous vessels within a human being. Those skilled in the art will recognize the benefits of applying the present invention to similar fields not discussed herein.

BACKGROUND OF THE INVENTION

Stroke is one of the leading causes of death in the industrialized world. In the United States alone stroke is currently the third most common cause of death and is the leading cause of permanent adult disability. With over 500,000 new cases reported each year and over 3 million living stroke victims (mostly disabled), it is clear that stroke is a major medical ailment that, if solved, could relieve the pain and suffering of many people.

An ischemic stroke is the result of thrombi that is free-floating within a person's vasculature or has formed at a particular site within the vasculature. When the free-floating thrombi passes into a vessel that is smaller than the thrombi, the thrombi occludes the vessel and prevents blood from reaching tissues downstream. Similarly, thrombi that has formed at a site can grow large enough to completely occlude the vessel. While occlusion of a blood vessel is always of concern, occlusion of vessels that supply the brain is catastrophic if not treated within a short period of time.

When a cerebral vessel becomes blocked, there is an area of tissue perfused by the vessel called the ischemic core which immediately sustains irreversible damage. There is also an area of tissue around the core called the penumbra. The penumbra is an area of tissue that stops functioning but is kept alive by blood flowing through collateral vessels. While the ischemic core is destroyed, rapid restoration of blood flow to the penumbra can minimize the damage caused by an ischemic stroke. Studies have now shown that damage to the penumbra progresses gradually over time until about six hours from the beginning of the ischemic stroke. After six hours any tissue not fully vascularized by collateral vessels is also permanently destroyed. It is therefore crucial that strokes be treated as quickly as possible.

One technique used for revascularization is systemic thrombolytic therapy. This technique uses intravenous injection of a relatively large quantity of liquid thrombolytic agent to lyse the thrombus. While moderately successful, only a portion of the thrombolytic agent reaches the thrombus. The remaining portion of thrombolytic agent may cause hemorrhagic complications throughout the rest of the body. A second technique is called intra-arterial thrombolytic therapy. This second technique delivers a thrombolytic agent to the thrombus site using a system consisting of a guidewire and a microcatheter used through a diagnostic or guide catheter. Intra-arterial thrombolytic therapy provides the ability to deliver thrombolytic agent to the site of the thrombus, use less thrombolytic agent then systemic thrombolytic therapy, and allows mechanical manipulation of the thrombus and angiographical monitoring of the revascularization process.

Using intra-arterial thrombolytic therapy requires a physician to insert a guidewire into a patient's vasculature through a microcatheter or guide catheter. The wire is then moved into position just proximal to the site of the thrombus. Once the wire is in place, the physician advances the microcatheter over the guide wire and to the site of occlusion. The wire is then removed and thrombolytic agents are infused directly to the point of occlusion. This technique has proven more successful than systemic infusion of large quantities of a thrombolytic agent. However, this technique also has its own limitations. The most important of these limitations is that placing the wire, delivering the microcatheter over the wire and then removing the wire requires time and in that time brain tissue is dying.

In addition to the limitations of prior art systems, there are many complications that result from an ischemic stroke that have not been addressed by prior art systems. Many of these complications can be grouped into two broad categories, ischemic damage and reperfusion injury. Ischemic damage is metabolic damage that occurs due to a lack of blood flow to cells. Another complication not addressed by prior art systems is reperfusion injury, that is cell damage caused by a cascade of chemical reactions upon the restoration of blood flow.

Accordingly, a therapeutic infusion device which could effectively cross a thrombus lodged in a cerebral artery, deliver a thrombolytic agent to the thrombus and a neuroprotective drug to the distal side of the thrombus simultaneously would be highly advantageous. It would be of further advantage to provide a therapeutic infusion device capable of being advanced to the site of thrombus and cross the thrombus without the need for a separate guide wire.

SUMMARY OF THE INVENTION

The present method overcomes the deficiencies of the prior art by providing a therapeutic infusion device that is flexible enough to be steered within the tortuous anatomy of the human vasculature, including the brain, and still have the ability to be pushed across a thrombotic occlusion without the use of a guidewire. In addition, the therapeutic infusion device used has two separate sets of infusion ports each communicating with a separate lumen. These sets of infusion ports allow a physician to infuse therapeutic or diagnostic fluids on either side of the thrombus, into the thrombus and onto either sides of the thrombus, or onto both sides of the thrombus simultaneously.

A first embodiment of the therapeutic infusion device has a long body having first lumen which connects a first set of holes near the distal end of the therapeutic infusion device to a port at the proximal end of the therapeutic infusion device. Similarly, a second lumen connects a second set of holes, located proximal to the first set of holes, to another port at the proximal end of the therapeutic infusion device. The sets of holes are positioned such that one set is 2–10 cm from the other set, thereby providing sets of holes which can be located on either side or within thrombus. The lumens of the therapeutic infusion device may be coaxial along the entire length of the device, side by side along the entire length, or may change from coaxial to side by side within the therapeutic infusion device. The therapeutic infusion device may also include a core wire located in the distal portion of one of the lumens. The core wire may be affixed at its proximal end to the interior of the therapeutic infusion device within one of the lumens. The distal end of the core wire may also be surrounded by an atraumatic tip where the tip may be a polymer tip or a spring tip. Finally, the atraumatic tip may also be bonded to the distal-most end of the therapeutic infusion device.

A method of the invention comprises using embodiments of the therapeutic infusion device described above in several different ways based on the user's needs for contrast agents, thrombolytic agents, and therapeutic drugs. In a first embodiment of the method a diagnostic or guide catheter may be inserted into the vasculature. The therapeutic infusion device may then be inserted through and beyond the distal end of the diagnostic catheter. The therapeutic infusion device may further be advanced until the distal set of holes is on the distal side of the thrombus and the proximal set of holes is on the proximal side or within the thrombus. A neuroprotective drug may then be infused through the device and out the distal set of holes while a thrombolytic agent is infused through the device and out the proximal set of holes providing therapy to the brain distal of the thrombus while dissolving the thrombus.

In another embodiment, a diagnostic or guide catheter may be inserted into the vasculature. The therapeutic infusion device may then be inserted through and beyond the distal end of the diagnostic catheter. Before the therapeutic infusion device contacts the thrombus a contrast agent may be infused through one or both of the lumens simultaneously and thereby make it possible to angiographically view the vasculature proximal of the thrombus. The therapeutic infusion device may then be further advanced such that a set of holes is placed on each side of the thrombus as described above, or the therapeutic infusion device may be advanced to the point where the distal set of holes is embedded in the thrombus and the proximal set of holes is proximal to the thrombus. A thrombolytic agent may then be infused through the distal set of holes and directly into the thrombus while a contrast agent is infused through the proximal set of holes. This method makes it possible to angiographically view the dissolution of the thrombus.

DETAILED DESCRIPTION OF THE INVENTION

The following detailed description should be read with reference to the drawings in which like elements in different drawing are numbered identically. The drawings, which are not necessarily to scale, depict selected embodiments and are not intended to limit the scope of the invention.

Example of constructions, materials, dimensions, and manufacturing processes are provided for selected elements. All other elements employ that which is known to those skilled in the field of the invention. Those skilled in the art will recognize that many of the examples provided have suitable alternatives that may also be used.

Figure 1:
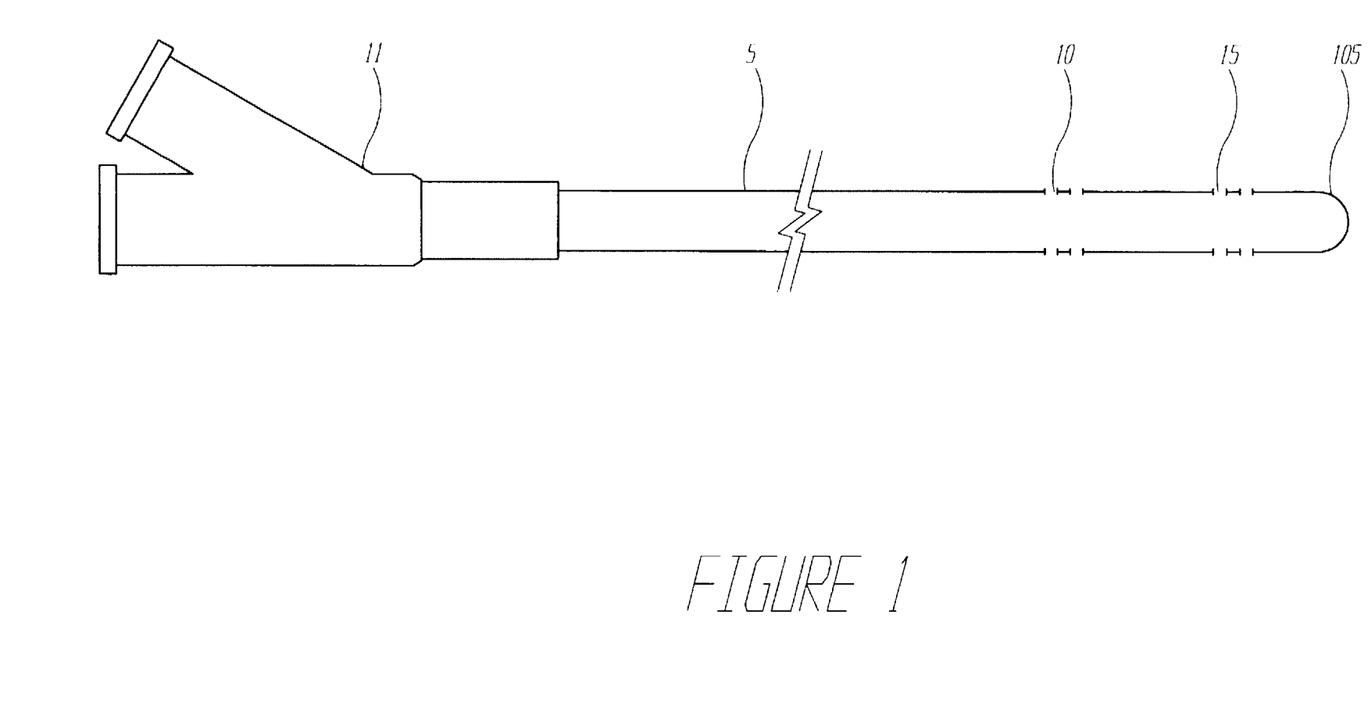
FIG. 1 is a side view of a generic therapeutic infusion device.

As shown in FIG. 1 a manifold 11 is attached to the proximal end of elongate body 5. Manifold 11 is a common manifold as is well known to those skilled in the art and provides a luer connection to elongate body 5. Near the distal end of elongate body 5 are proximal side holes 10 and distal side holes 15. Proximal side holes 10 perforate elongate body 5 proximal of distal side holes 15. Both proximal side holes 10 and distal side holes 15 have separate fluid communication paths within elongate body 5 to manifold 11 and are preferably about 2–10 cm apart. At the distal end of elongate body 5 there may be an atraumatic tip 105 suitable for reducing trauma to the interior of the human vasculature.

Figure 2:
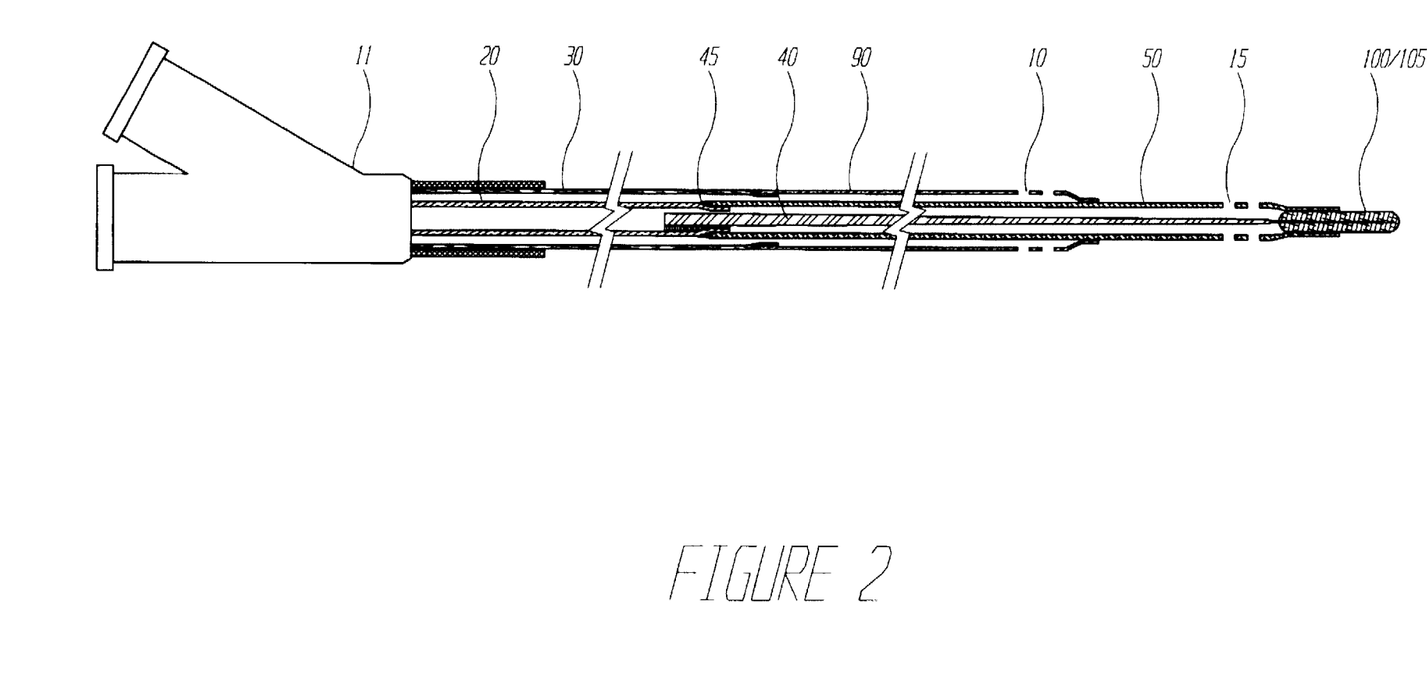
FIG. 2 is a side view of a first embodiment of the therapeutic infusion device.

In a first embodiment of the therapeutic infusion device as shown in FIG. 2, manifold 11 provides a luer connection to the proximal end of inner hypo tube 20 and outer tube 30 which may be adhesively bonded with a cyanoacrylate adhesive, preferably Loctite 460™. This first embodiment of the therapeutic infusion device may have an inner lumen that is constructed in two parts. The first part of the inner lumen is inner hypo tube 20. Inner hypo tube 20 may be adhesively bonded with a cyanoacrylate adhesive, such as Loctite 460™, at its proximal end to manifold 11 and at its distal end to the proximal end of inner shaft 50. Inner hypo tube 20 can be made of any medical grade alloy but is preferably stainless steel with an outer diameter of about 0.015–0.035 inches and a wall thickness of about 0.002–0.005 inches.

The second part of the inner lumen is inner shaft 50. The proximal end of inner shaft 50 may be adhesively bonded with an epoxy, such as Tracon BA 21350™, to the distal end of inner hypo tube 20 at inner bond 45. Inner shaft 50 can be made of polyethylene, polyurethane, a polyethylene/polyurethane blend or coextrusion, or any other suitable medical grade polymer. In addition, inner shaft 50 may also incorporate a fiber braid to make shaft 50 stronger or radio-opaque fillers in the polymer mix to make inner shaft 50 visible under fluoroscopy. Preferably inner shaft 50 has an inner diameter of about 0.010–0.035 inches and wall thickness of about 0.002–0.005 inches.

Near the distal end of inner shaft 50 there are distal side holes 15 which complete a first fluid path from manifold 11 along the interior of inner hypotube 20 and inner shaft 50 to distal side holes 15. Distal side holes 15 are placed around the circumference of inner shaft 50. There may be at least one distal side hole 15 and preferably about 4–12 proximal side holes 15 which are about 0.005–0.010 inches in diameter and cover up to about 10.0 cm of the distal end of inner shaft 50. Holes 15 may be made in a variety of ways common to those skilled in the art. Some ways that holes 15 may be made include drilling, laser cutting, heat forming, or water-jet cutting and preferably may be made by punching.

Inner shaft 50 may be adhesively or solvently bonded to an atraumatic tip 105 using and epoxy such as Tracon BA 2135D™. The bond between inner shaft 50 and atraumatic tip 105 may be made such that it creates a fluid-tight seal or allows fluid to be discharged through the distal end of the therapeutic infusion device. Atraumatic tip 105 may be a spring tip, where the spring tip may be a spring tip as is commonly recognized to those skilled in the art, or preferably atraumatic tip 105 is a polymer tip 100. In a preferred embodiment polymer tip 100 is composed of a medical grade polymer and may be loaded with a tungsten powder or other suitable radio-opaque filler to make polymer tip 100 visible under fluoroscopy. Polymer tip 100 has an outer diameter of about 0.010–0.035 inches and surrounds the distal end of core wire 40.

Core wire 40 may be made of any suitable medical grade alloy but is preferably stainless steel or Nitinol. Core wire 40 tapers from a proximal diameter of about 0.005–0.020 inches to a distal diameter of about 0.002–0.010 inches. The proximal end of core wire 40 may be brazed to the interior of inner hypotube 20 at inner bond 45. The distal end of core wire 40 is surrounded by polymer tip 100 and is located inside of inner shaft 50. Further, polymer tip 100 may be bent, prior to use, into any shape that the user desires.

Coaxially surrounding inner hypotube 20 and inner shaft 50 is a two part outer composed of proximal outer hypotube 30 and distal outer tube 90. The proximal end of outer hypotube 30 may be adhesively bonded with a cyanoacrylate adhesive such as Loctite 460™, to manifold 11. Proximal outer 30 can be made of polyimide, urethane coated polyimide, low density polyethylene(LDPE), a LDPE/urethane blend, or other suitable medical grade polymer. Proximal outer 30 has an inner diameter of about 0.018–0.050 inches and a wall thickness of about 0.015–0.006 inches.

The distal end of outer hypotube 30 is preferably adhesively bonded with an epoxy, such as Tracon BA 2135D™, to the proximal end of distal outer 90 distal of inner bond 45. Distal outer tube 90 may made of polyimide, urethane coated polyimide, LDPE, or an LDPE/urethane blend. Distal outer tube 90 may have an inner diameter of about 0.018–0.050 inches and a wall thickness of about 0.015–0.006 inches. Distal outer tube 90 may be heat, solvent, or adhesively bonded with an epoxy, such as Tracon BA 2135D™, to inner shaft 50 proximal of distal side holes 15. The bond may completely surround inner shaft 50 or only partially surround inner shaft 50. If the bond only partially surrounds inner shaft 50, another fluid outlet, from the annular space between distal out tube 90 and inner shaft 50, is provided to the exterior of the therapeutic infusion device. In another embodiment of the therapeutic infusion device, all or some portion of distal outer tube 90 or inner shaft 50 may be coated with a lubricious coating, preferably a hydrophilic coating.

Near the distal end of distal outer tube 90 are proximal side holes 10 which complete a second fluid path from manifold 11, between outer hypotube 30 and inner hypotube 20, between distal outer 90 and inner shaft 50, to proximal side holes 10. Proximal side holes 10 are spaced around the circumference of distal outer tube 90. There may be at least one proximal side hole 10 and preferably about 4–12 proximal side holes 10 which are about 0.005–0.010 inches in diameter and cover up to about 10.0 cm of the distal end of distal outer tube 90. Holes 10 may be made in a variety of ways common to those skilled in the art. Some ways that holes 10 may be made include drilling, laser cutting, heat forming, or water-jet cutting and preferably may be made by punching.

Figure 3A:
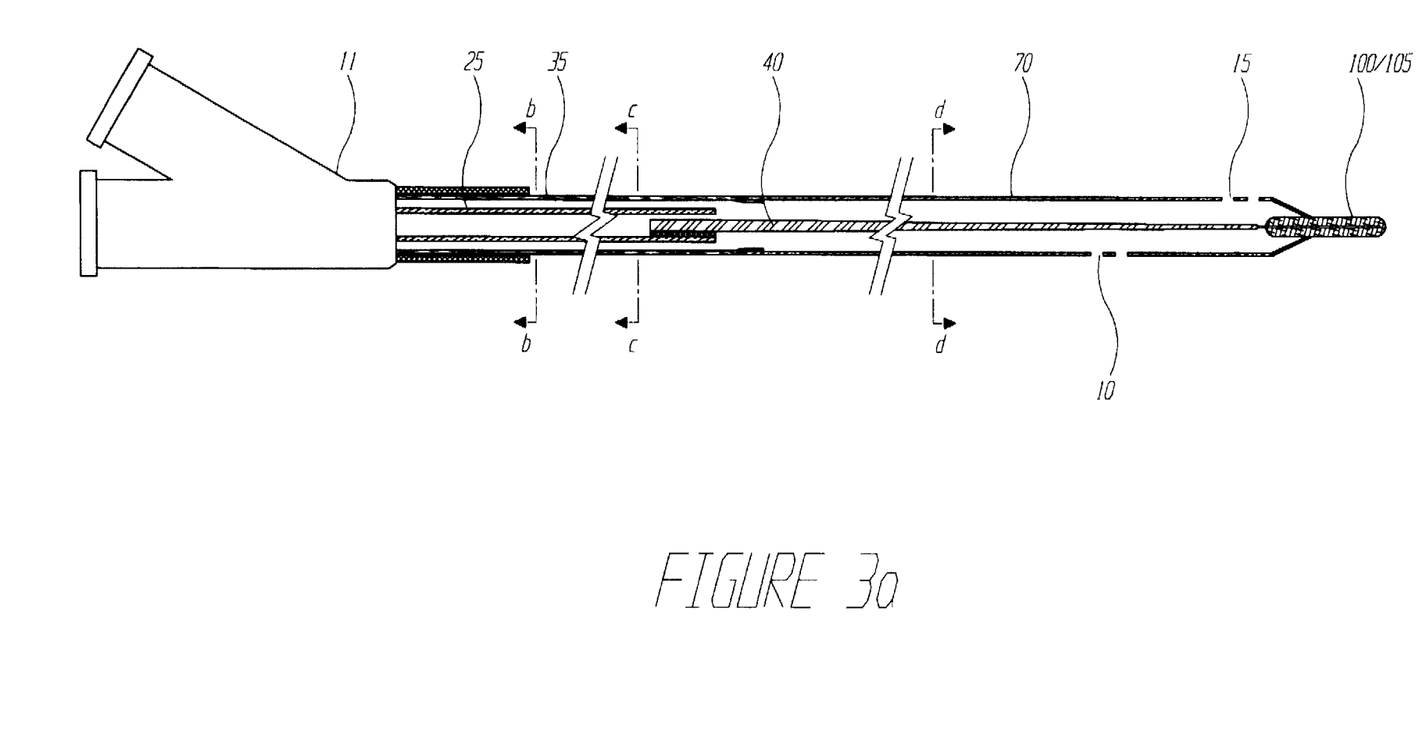
FIG. 3a is a side view of a second embodiment of the therapeutic infusion device.

FIG. 3a depicts a second embodiment of the therapeutic infusion device where manifold 11 provides a luer connection to the proximal end of proximal inner tube 25. Proximal inner tube 25 is a stiff hypotube made of any suitable medical grade alloy and preferably of stainless steel. Proximal inner tube 25 may have an inner diameter of about 0.015–0.025 inches and a wall thickness of about 0.002–0.005 inches.

Figure 3B:
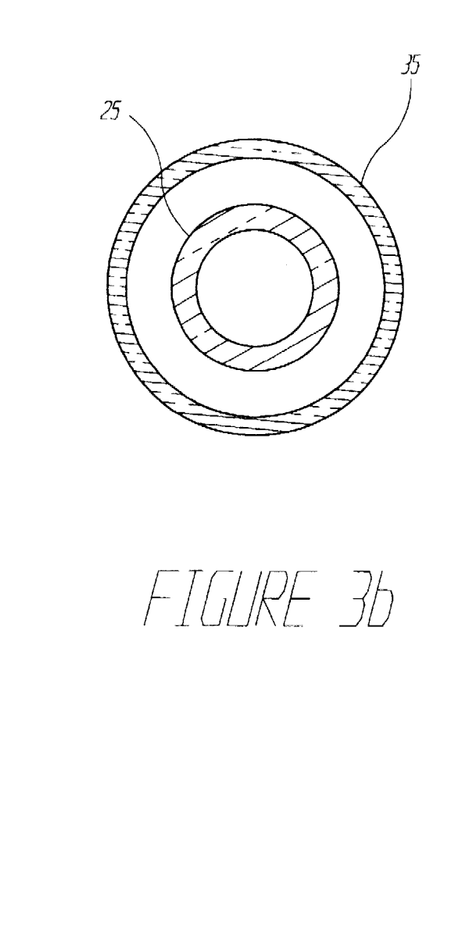
FIG. 3b is a cross sectional view of the embodiment of FIG. 3a taken along lines b—b.

Surrounding proximal inner 25 is proximal outer tube 35. Proximal outer 35 may be made of polyimide or urethane coated polyimide and may have an outer diameter of about 0.030–0.050 inches and a wall thickness of about 0.015–0.006 inches. The proximal end of proximal outer 35 may be adhesively bonded with a cyanoacrylate adhesive, such as Loctite 460™, to manifold 11. As seen in FIG. 3a, near manifold 11 proximal outer 35 and proximal inner tube 25 are coaxial. FIG. 3b further shows that the relative position of proximal outer 35 to proximal inner tube 25 translates from coaxial to a dual lumen configuration proximal to distal.

Figures 3C, 3D:
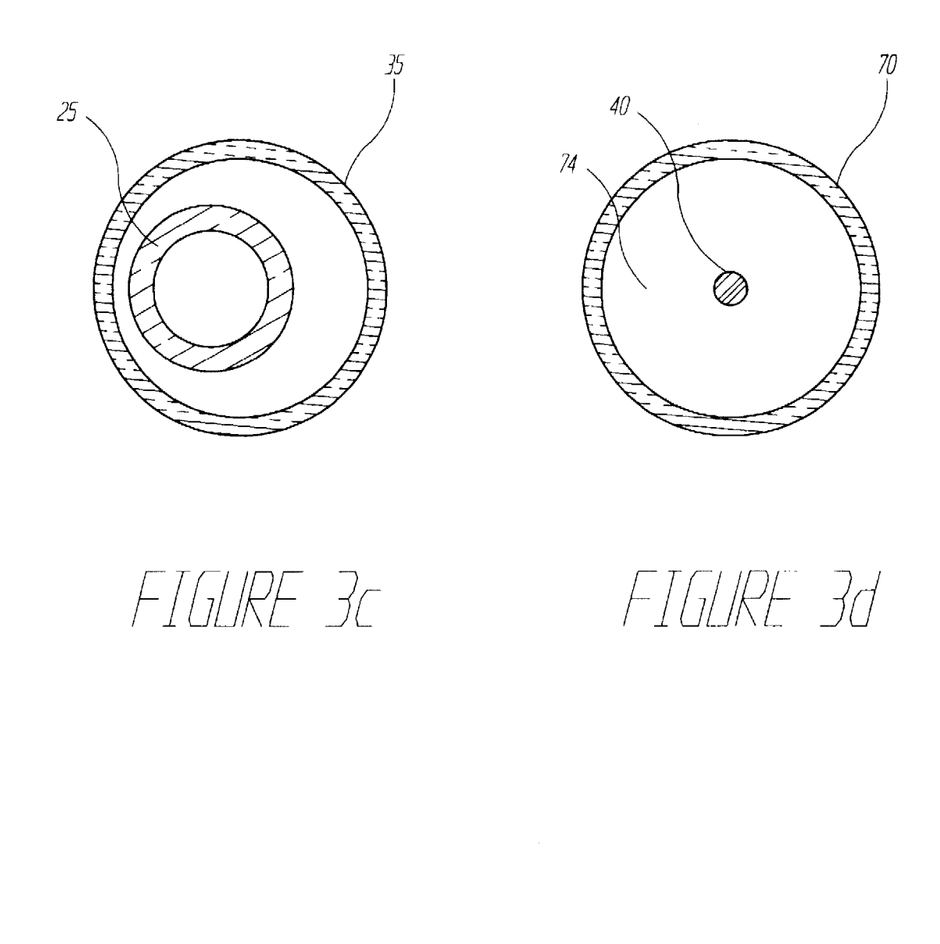
FIG. 3c is a cross sectional view of the embodiment of FIG. 3a taken along lines c—c.
FIG. 3d is a cross sectional view of the embodiment of FIG. 3a taken along lines d—d.

The distal end of proximal outer 35 may be adhesively bonded with an epoxy, such as Tracon BA 2135D™, to the proximal end of distal tube 70. Distal tube 70 is a dual lumen tube which provides two distinct fluid lumens. Distal tube 70 may be made of urethane, LDPE, or a LDPE/urethane mix where the outer diameter may be about 0.025–0.045 inches. FIG. 3d shows a lateral cross section of distal tube 70 with a first lumen 72 which is in fluid communication with the interior of proximal inner tube 25 and a second lumen 74 which is in fluid communication with the interior of proximal outer 35.

Near the distal end of distal tube 70 are distal side holes 15 which complete a first fluid path from manifold 11 along the interior of proximal inner tube 25 and first lumen 72 to distal side holes 15. Distal side holes 15 perforate distal tube 70 and provide a first fluid path from manifold 11, within proximal inner tube 25, through first lumen 72 to distal side holes 15. There may be at least one distal side hole 15 and preferably about 4–12 distal side holes 15 which are about 0.005–0.010 inches in diameter and cover up to about 10.0 cm of distal tube 70. Proximal to distal side holes 15 are proximal side holes 10 which complete a second fluid path from manifold 11, between proximal outer 35 and proximal inner tube 25, and through lumen 74 to proximal side holes 10. Proximal side holes 10 also perforate distal tube 70. There may be at least one proximal side hole 10 and preferably about 4–12 proximal side holes 10 which are about 0.005–0.010 inches in diameter and cover up to about 10.0 cm of the distal end of distal tube 70.

Traversing lumen 72 is core wire 40. Core wire 40 may be brazed to proximal inner tube 25 near the distal end of proximal inner tube 25. Surrounding the distal end of core wire 40 is an atraumatic tip 105. As described above, atraumatic tip 105 may be any atraumatic tip commonly known to those skilled in the art. In a preferred embodiment of the therapeutic infusion device, the distal end of distal tube 70 may be heat shrunk to polymer tip 100. Polymer tip 100 surrounds the distal end of core wire 40. The bond between distal tube 70 and polymer tip 100 may be made such that it creates a fluid-tight seal or allows fluid to be discharged through the distal end of the therapeutic infusion device. Polymer tip 100 may be composed of a medical grade polymer and may be loaded with a tungsten powder or other suitable radio-opaque filler so as to be visible under fluoroscopy. Polymer tip 100 has an outer diameter of about 0.010–0.038 inches. Alternatively, a device using a single lumen design may also be used to perform some portions of the following methods of use.

In use either embodiment of the therapeutic infusion device may, depending on the user's preference, be used in the following manner. An diagnostic or guide catheter is inserted into a patient's vasculature and advanced to a position within the vasculature in the vicinity of the patient's neck. The therapeutic infusion device is then advanced through the diagnostic catheter. When proximal side holes 10 and distal side holes 15 extend beyond the end of the diagnostic catheter, it is possible to infuse a contrast agent through either or both sets of holes. Then using standard angiography, digital subtraction angiography, or road mapping, it is possible to visualize the structure of the vasculature and begin to identify any occlusions. If further treatment is indicated the therapeutic infusion device can be advanced further into the patient's vasculature while the diagnostic catheter remains in place.

In a situation where the source of occlusion is determined to be thrombus resulting in a stroke, the therapeutic infusion device may be advance to a point proximal to the thrombus and contrast infused through one of the sets of side holes. Selective angiography may then be done to determine the degree of occlusion and the extent of peripheral vascularization. If treatment of the thrombus is needed, a thrombolytic agent may be infused through the other set of side holes. Alternatively, the therapeutic infusion device may be further advanced to a point where the distal side holes 15 are on the distal side of or within the thrombus and the proximal side holes 10 are on the proximal side of the thrombus.

With a set of side holes on each side of the thrombus, there are many combinations of contrast agents, thrombolytic agents, neuroprotective drugs, and other drugs that may be infused through the side holes. In addition, suction could also be added to one or both of the lumens and used in combination with any of the fluids contemplated herein. One advantageous combination may be to infuse a neuroprotective agent like an anti-edema agent, glutamate antagonists, calcium channel blockers, oxygen radical scavengers, lipid peroxidation inhibitors, gangliosides, NOS antagonists, or a cool fluid through the distal side holes 15. Simultaneously a thrombolytic agent, such as, streptokinase, urokinase, prourokinase, tissue plasminogen activator, or recombinant tissue plasminogen activator may be infused through the proximal side holes 10. This combination allows downstream tissue to be protected while the thrombus is being dissolved.

Another advantageous combination may be to position the distal side holes 15 within the thrombus and thereby position the proximal side holes 10 proximal of the thrombus. A thrombolytic agent as described previously may then be infused through distal side holes 15 while a contrast agent is infused through proximal side holes 10. This combination allows the thrombus to be dissolved while dissolution of the thrombus is angiographically monitored.

Yet another advantageous combination may be to position the proximal side holes 10 within the thrombus. A thrombolytic agent as described previously may then be infused through proximal side holes 10 while a neuroprotective agent or a contrast agent is infused through distal side holes 15.

While a detailed description of use of the therapeutic infusion device has been performed for use in the head, these same methods of use may be used in any part of the body where thrombus might lodge. Further the specification describes the preferred designs, materials, methods of manufacture and methods of use and those skilled in the art will appreciate the scope and spirit of the invention with reference to the appended claims.

I claim:

1. A method of treating thrombus that is lodged in a human vasculature, comprising the steps of:
   i. providing a device having:
      (a) an elongate body with a distal and a first and a second lumen therethrough;
      (b) a first at least one opening near the distal end of the elongate body, the first at least one opening in fluid communication with the first lumen; and
      (c) a second at least one opening proximal to the first at least one opening, the second at least one opening in fluid communication with the second lumen;
   ii. advancing the device through the vasculature such that the first at least one opening is distal to the thrombus and the second at least one opening is proximal to the thrombus;
   iii. infusing a first fluid through the first lumen, out the first at least one opening and into the vasculature distal of the thrombus; and
   iv. infusing a second fluid through the second lumen, out the second at least one opening and into the vasculature proximal of the thrombus.

2. The method of treating thrombus as in claim 1 wherein the device includes a core wire having a proximal end and a distal end, the proximal end of the core wire affixed to the elongate body within the first lumen and the distal end of the core wire affixed to the elongate body within a distal end of the first lumen.

3. The method of treating thrombus as in claim 2 wherein the distal end of the core wire includes an atraumatic tip.

4. The method of treating thrombus as in claim 2 wherein the first lumen has a proximal portion, a distal portion and an axis and the second lumen has a proximal portion, a distal portion and an axis, the proximal portion of the first lumen disposed coaxial to the proximal portion of the second lumen and the axis of the distal portion of the first lumen disposed adjacent the axis of the distal portion of the second lumen.

5. A method of diagnosing and treating thrombus that is lodged in a human vasculature comprising the steps of:
   i. providing a device having:
      (a) an elongate body with a distal end and a first and second lumen therethrough;
      (b) a first at least one opening near the distal end of the elongate body, the first at least one opening in fluid communication with the first lumen; and
      (c) a second at least one opening proximal to the first at least one opening, the second at least one opening in fluid communication with the second lumen;
   ii. advancing the device through the vasculature such that the first at least one opening is embedded in the thrombus; and
   iii. infusing a thrombolytic agent out of the first at least one opening such that the thrombus is dissolved or broken into small pieces.

6. The method of diagnosing and treating thrombus as in claim 5 further comprising the step of:
   infusing a fluid out of the second at least one opening and into the vasculature proximal to the thrombus.

7. The method of diagnosing and treating thrombus as in claim 6 wherein the fluid is a contrast agent.

8. The method of diagnosing and treating thrombus as in claim 6 wherein the fluid is a thrombolytic agent.

9. The method of diagnosing and treating thrombus as in claim 6 wherein the fluid is a neuroprotective agent.

10. A method of diagnosing and treating thrombus that is lodged in a human vasculature comprising the steps of:
    i. providing a device having:
       (a) an elongate body with a distal end and a first and second lumen therethrough;
       (b) a first at least one opening located near the distal end of the elongate body, the first at least one opening in fluid communication with the first lumen; and
       (c) a second at least one opening located proximal to the first at least one opening, the second at least one opening in fluid communication with the second lumen;
    ii. advancing the device through the vasculature such that the second at least one opening is embedded in the thrombus and the first at least one opening is distal to the thrombus; and
    iii. infusing a thrombolytic agent out of the second at least one opening such that the thrombus is dissolved or broken into small pieces.

11. The method of diagnosing and treating thrombus as in claim 10 further comprising the step of:
    infusing a fluid through the first lumen, out the first at least one opening and into the vasculature distal to the thrombus.

12. The method of diagnosing and treating thrombus as in claim 11 wherein the fluid is a contrast agent.

13. The method of diagnosing and treating thrombus as in claim 11 wherein the fluid is a thrombolytic agent.

14. The method of diagnosing and treating thrombus as in claim 11 wherein the fluid is a neuroprotective agent.

* * * * *

UNITED STATES PATENT AND TRADEMARK OFFICE
CERTIFICATE OF CORRECTION

PATENT NO. : 5,782,797
DATED : July 21, 1998
INVENTOR(S) : SCHWEICH JR. et al.

It is certified that error appears in the above-identified patent and that said Letters Patent is hereby corrected as shown below:

At column 4, line 60, "Nitinol" should be --Nitinol™--.

At column 5, line 11, "0.015" should be --0.0015--; at line 19, "0.015" should be --0.0015--; at line 58, "0.015" should be --0.0015--.

At column 7, line 50, claim 1, insert --end-- after "distal".

Signed and Sealed this

Twelfth Day of January, 1999

Attest:

Attesting Officer

Acting Commissioner of Patents and Trademarks